(12) United States Patent
Spruit et al.

(10) Patent No.: US 11,589,751 B2
(45) Date of Patent: Feb. 28, 2023

(54) METHOD AND APPARATUS FOR EARLY CARIES DETECTION

(71) Applicant: KONINKLIJKE PHILIPS N.V., Eindhoven (NL)

(72) Inventors: Johannes Hendrikus Maria Spruit, Waalre (NL); Cristian Nicolae Presura, Veldhoven (NL); Steven Charles Deane, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 58 days.

(21) Appl. No.: 16/625,225

(22) PCT Filed: Jun. 21, 2018

(86) PCT No.: PCT/EP2018/066576
§ 371 (c)(1),
(2) Date: Dec. 20, 2019

(87) PCT Pub. No.: WO2018/234447
PCT Pub. Date: Dec. 27, 2018

(65) Prior Publication Data
US 2020/0138297 A1    May 7, 2020

Related U.S. Application Data

(60) Provisional application No. 62/522,733, filed on Jun. 21, 2017.

(51) Int. Cl.
*A61B 5/00* (2006.01)
*A61C 19/04* (2006.01)

(52) U.S. Cl.
CPC ............ *A61B 5/0088* (2013.01); *A61C 19/04* (2013.01)

(58) Field of Classification Search
CPC ......... A61C 19/04; A61B 5/0082; A61B 6/00; A61B 5/0088
(Continued)

(56) References Cited

U.S. PATENT DOCUMENTS

| 6,254,385 B1 * | 7/2001 | Jung | .................... A61B 5/0088 356/405 |
| 6,726,476 B2 * | 4/2004 | Jung | .................... A61B 5/0088 433/26 |

(Continued)

FOREIGN PATENT DOCUMENTS

| EP | 950228 B1 | 5/2004 |
| JP | 2011167308 A | 9/2011 |
| WO | 2014105521 A1 | 7/2014 |

OTHER PUBLICATIONS

International Search Report and Written Opinion, International Application No. PCT/EP2018/066576, dated Sep. 6, 2018.
(Continued)

*Primary Examiner* — Nicholas D Lucchesi

(57) ABSTRACT

A method (300) for detecting one or more caries using an imaging device (10), the method including the steps of: (i) directing (320) light from a first light source (12) toward a tooth (40); (ii) measuring (340), with an optical sensor (16), transmission of light from the first light source through the tooth; (iii) directing (330) light from a second light source (14) toward the tooth, wherein the second light source directs light at the tooth at a different angle relative to the first light source; (iv) measuring (350), with the optical sensor, reflectance from the tooth of light from the second light source; (v) comparing (360) the measured transmission to the measured reflectance; and (vi) determining (370), based at least in part on said comparison, whether a caries is present in the tooth.

15 Claims, 11 Drawing Sheets

(58) Field of Classification Search
USPC .......................................................... 433/29
See application file for complete search history.

(56) References Cited

U.S. PATENT DOCUMENTS

| | | | | |
|---|---|---|---|---|
| 7,403,285 | B2* | 7/2008 | Jung | A61B 5/0088 356/326 |
| 7,702,139 | B2* | 4/2010 | Liang | A61B 1/00186 382/128 |
| 7,862,335 | B2* | 1/2011 | Berube-Lauziere | A61B 5/0088 433/29 |
| 8,077,949 | B2* | 12/2011 | Liang | G01B 11/285 382/128 |
| 8,270,689 | B2* | 9/2012 | Liang | A61B 5/0066 382/128 |
| 8,297,971 | B2* | 10/2012 | Berube-Lauziere | A61B 5/0088 433/29 |
| 8,447,087 | B2* | 5/2013 | Wong | G01B 11/2441 382/128 |
| 8,605,974 | B2* | 12/2013 | Liang | G01J 3/02 382/128 |
| 8,647,119 | B1 | 2/2014 | Nagai | |
| 9,060,690 | B2* | 6/2015 | Liang | G01J 3/0213 |
| 9,463,081 | B2* | 10/2016 | Urakabe | A61B 1/247 |
| 10,070,791 | B2* | 9/2018 | Liang | A61B 1/0607 |
| 10,213,113 | B2* | 2/2019 | Islam | A61B 5/0075 |
| 10,874,304 | B2* | 12/2020 | Islam | A61B 5/1455 |
| 10,944,953 | B2* | 3/2021 | Babayoff | A61C 19/04 |
| 2002/0093655 | A1 | 7/2002 | Everett et al. | |
| 2003/0035107 | A1* | 2/2003 | Overbeck | G01J 3/0208 356/405 |
| 2005/0181333 | A1* | 8/2005 | Karazivan | A61B 5/0088 433/215 |
| 2006/0223032 | A1 | 10/2006 | Fried et al. | |
| 2007/0054242 | A1* | 3/2007 | Jung | G01J 3/508 433/213 |
| 2007/0105069 | A1 | 5/2007 | Yamagishi | |
| 2007/0134615 | A1 | 6/2007 | Lovely | |
| 2008/0056551 | A1 | 3/2008 | Wong et al. | |
| 2008/0063998 | A1* | 3/2008 | Liang | A61B 5/4547 433/29 |
| 2010/0060880 | A1 | 3/2010 | Bloss | |
| 2011/0221880 | A1 | 9/2011 | Liang et al. | |
| 2012/0237890 | A1* | 9/2012 | Liang | G01N 21/4795 433/29 |
| 2013/0302746 | A1* | 11/2013 | Liang | G01J 3/0224 433/29 |
| 2015/0245770 | A1* | 9/2015 | Liang | A61B 5/0088 433/29 |
| 2015/0305670 | A1 | 10/2015 | Spruit et al. | |
| 2018/0296098 | A1* | 10/2018 | Islam | A61B 5/7257 |
| 2020/0138297 | A1* | 5/2020 | Spruit | A61B 5/4547 |

OTHER PUBLICATIONS

Karlsson, L., "Caries Detection Methods Based on Changes in Optical Properties between Healthy and Carious Tissue", International Journal of Dentistry, Oct. 2009.

Simon, Jacob C. et al, "Assessment of cavitation in artificial approximal dental lesions with near-IR imaging", Progress in Biomedical Optics and Imaging, vol. 10044, Lasers In Dentistry XXIII, Jan. 29, 2017, San Francisco, CA.

* cited by examiner

METHOD AND APPARATUS FOR EARLY CARIES DETECTION

This application is the U.S. National Phase application under 35 U.S.C. § 371 of International Application No. PCT/EP2018/066576, filed on 21 Jun. 2018, which claims the benefit of U.S. Provisional Application No. 62/522,733, filed 21 Jun. 2017. These applications are hereby incorporated by reference herein.

FIELD OF THE INVENTION

The present disclosure relates generally to systems and methods for detecting caries using the transmission of light through a tooth and the reflectance of light from the tooth as detected by an imaging device.

BACKGROUND

Proper tooth brushing and flossing technique, including length and coverage of brushing and flossing, helps ensure long-term dental health. Many dental problems are experienced by individuals who do not regularly brush and floss their teeth, or who do so inadequately. Decay of tooth surfaces, called caries, can occur when bacteria break down the hard tissues of the teeth. If caries are allowed to proceed without treatment, they will further erode the tooth and will result in pain, infection, and possible loss of the tooth.

Accordingly, while it is preferable to prevent caries, it is advantageous to detect caries as early as possible so that they may be treated before substantial damage to the tooth occurs. Early caries are smaller, have done less damage to the tooth, and are often easily treated by a dental professional in a single visit. Since many people have a fear of dental professionals, or rarely schedule visits with a dental professional with a significant amount of time between these visits, it would be advantageous to have a method for early caries detection outside the dental professional's office. However, current methods for the early detection of caries outside the dental professional's office are unsatisfactory and often fail to identify caries.

X-ray imaging is one technique for caries detection, but is not suitable for home applications. Another technique for early caries detection is fiber optic trans-illumination (FOTI) in which the tooth is inspected by illumination with visible light. Other optical techniques use infrared light for caries detection, since a caries is significantly less transparent due to scattering of infrared light at this location. Among other limitations, FOTI techniques suffer from scattering of light by the teeth, resulting in bad contrast. Stained teeth also result in unreliable detection of caries. Accordingly, existing methods for detecting caries are expensive, potentially dangerous, and/or suffer from artifacts produced by light scattering and stained teeth or dental work.

Accordingly, there is a continued need in the art for methods and systems for the effective and affordable early detection of caries.

SUMMARY OF THE INVENTION

The present disclosure is directed to inventive systems and methods for detecting one or more caries using an imaging device. Various embodiments and implementations herein are directed to an imaging device uses light transmission through and reflectance from a tooth to improve the detection of early caries while reducing artifacts. The imaging device emits light onto a tooth using two light sources at different angles relative to one another. The imaging device measures transmission of light from the first light source through the tooth, and measures reflectance from the tooth of light from the second light source. By comparing the measured transmission to the measured reflectance, the system determines whether a caries is present in the tooth.

Generally in one aspect, a method for detecting one or more caries using an imaging device is provided. The method includes the steps of: (i) directing light from a first light source toward a tooth; (ii) measuring, with an optical sensor, transmission of light from the first light source through the tooth; (iii) directing light from a second light source toward the tooth, wherein the second light source directs light at the tooth at a different angle relative to the first light source; (iv) measuring, with the optical sensor, reflectance from the tooth of light from the second light source; (v) comparing the measured transmission to the measured reflectance; and (vi) determining, based at least in part on said comparison, whether a caries is present in the tooth.

According to an embodiment, the method further include the step of obtaining, with the optical sensor, sensor data without light from the first and second light source, and wherein said comparing step further comprises subtracting the sensor data obtained without light from the measured transmission and/or the measured reflectance.

According to an embodiment, the optical sensor is an image sensor, wherein a transmission value and a reflection value are determined for each pixel of the image sensor, and wherein the determining step is based on a local variation of the transmission value and the reflection value for one or more pixels.

According to an embodiment, the method further includes the step of providing the determination of whether a caries is present in the tooth to the user.

According to an embodiment, the method further includes the step of communicating the determination of whether a caries is present in the tooth to a remote device.

According to an embodiment, the first or second light source further comprises an optical element.

According to an embodiment, at least one of the first or second light sources is a fluorescent light source.

According to an embodiment, the first and second light sources emit light having a wavelength between 900 and 1100 nm.

According to an aspect is an imaging device configured to detect one or more caries. The device includes: an optical sensor; a first light source configured to direct light toward a tooth such that the optical sensor measures transmission of light from the first light source through the tooth; a second light source configured to direct light toward the tooth such that the optical sensor measures reflectance from the tooth of light from the second light source; and a controller configured to: (i) compare the measured transmission to the measured reflectance; and (ii) determine, based at least in part on said comparison, whether a caries is present in the tooth.

According to an embodiment, the second light source directs light at the tooth at a different angle relative to the first light source.

According to an embodiment, the device further includes a user interface configured to provide the determination of whether a caries is present in the tooth to the user.

According to an aspect an imaging system is configured to provide a user with information about one or more caries. The system includes: an optical device comprising: (i) an optical sensor; (ii) a first light source configured to direct light toward a tooth such that the optical sensor measures transmission of light from the first light source through the tooth; (iii) a second light source configured to direct light toward the tooth such that the optical sensor measures reflectance from the tooth of light from the second light source; (iv) a controller configured to compare the measured transmission to the measured reflectance and determine, based at least in part on said comparison, whether a caries is present in the tooth; and (v) a communications module configured to communicate the determination; and the system further includes a user interface device comprising: (i) a communications module configured to receive the communicated determination; and (ii) a user interface configured to provide the determination of whether a caries is present in the tooth to the user.

As used herein for purposes of the present disclosure, the term "controller" is used generally to describe various apparatus relating to the operation of a stream probe apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and nonvolatile computer memory). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present disclosure discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of an imaging device configured to detect caries. More generally, Applicant has recognized and appreciated that it would be beneficial to provide a device that measures light transmission through and reflectance from a tooth to improve the detection of early caries while reducing artifacts. Accordingly, the methods and systems described or otherwise envisioned herein provide a system or device that emits light on a tooth using two light sources at different angles relative to one another. The device compares the measured transmission to the measured reflectance and, based on the relationship of the transmission to the reflectance, determines whether a caries is present in the tooth.

The embodiments and implementations disclosed or otherwise envisioned herein can be utilized with an imaging device. The imaging device may be, for example, an oral care device. Examples of suitable oral care devices include a toothbrush, an oral irrigator, an interproximal cleaning device, or other oral care device. However, the disclosure is not limited to these enumerated devices, and thus the disclosure and embodiments disclosed herein can encompass any imaging device.

Figure 1:
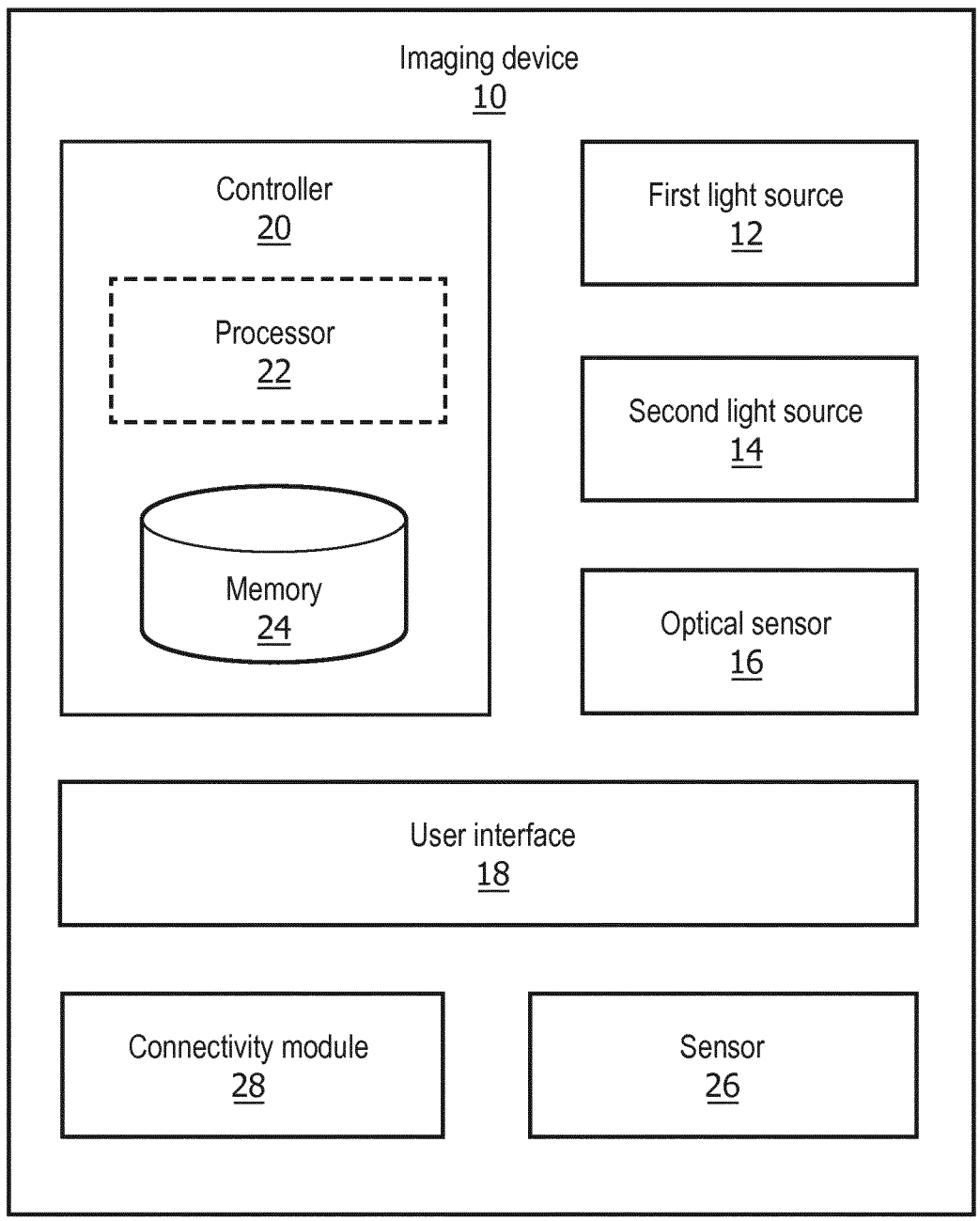
FIG. 1 is a schematic representation of an imaging device, in accordance with an embodiment.

Referring to FIG. 1, in one embodiment, is a schematic representation of an imaging device 10. According to an embodiment, the imaging device is a handheld device, at least a portion of which is configured to fit within a user's mouth to obtain sensor information about one or more teeth of that user. The imaging device may comprise, for example, a handle or body portion with an extension sized to fit within the user's mouth, the extension comprising one or more elements configured to obtain sensor information about one or more teeth of that user. According to an embodiment, imaging device 10 may be an oral care device such as a toothbrush, flosser, or other oral care device, and thus may comprise the one or more elements configured to obtain sensor information from the user's mouth. Accordingly, the oral care device may obtain information about early caries in the user's mouth, possibly while also being utilized to clean the user's teeth and/or oral tissues.

Imaging device 10 comprises a first light source 12 and a second light source 14, although additional light sources are possible. As described or otherwise envisioned herein, the first and second light sources are positioned or otherwise configured to illuminate the tooth from different angles. One or both of light sources 12 and 14 may be two or more light sources. According to an embodiment, one of the first and second light sources is positioned or otherwise configured to illuminate the tooth with light that will be utilized to obtain information about transmission of that light through the tooth, and the other of the first and second light sources is positioned or otherwise configured to illuminate the tooth with light that will be utilized to obtain information about reflectance of that light from the tooth.

In one arrangement of the present invention, the first and second light sources can be configured to emit infrared light having a wavelength range between 900 nm and 1100 nm, wherein 1000 nm may be an optimal wavelength. This results in optimum contrast for caries, while still being detectable by an affordable photo sensor. However, many other light wavelengths, including in ranges other than infrared, may be utilized to illuminate the user's teeth for caries detection.

As described herein, the first and second light sources can be configured to emit light simultaneously or sequentially. For example, the first and second light sources can emit a sustained, flash, or pulsing light beam simultaneously toward the tooth. As another example, first and second light sources can each emit a sustained, flash, or pulsing light beam sequentially or in an alternating or other pattern. For example, the first light source may emit a beam multiple times compared to the second light source, and vice versa. These variations require cooperation between the light sources, which can be coordinated by a controller or other component of the imaging device or system.

According to another embodiment, imaging device 10 comprises a single light source 12 configured to illuminate the tooth from at least two different angles. According to an embodiment, light source 12 is positioned or otherwise configured to illuminate the tooth with light that will be utilized to obtain information about transmission of that light through the tooth, and is positioned or otherwise configured to illuminate the tooth with light that will be utilized to obtain information about reflectance of that light from the tooth. For example, light source 12 can be positioned or otherwise configured to illuminate the tooth from a first angle, and the device can comprise a light path such as a light guide, mirror, or other mechanism to illuminate the tooth from a second angle. According to an embodiment, the light from the light source may be modified to provide light with different parameters to the two locations on the tooth. For example, the light may be modified with an optical switch or a modulator such that the image sensor can distinguish between captured images.

Imaging device 10 further comprises an optical sensor 16 configured to obtain light information from the tooth, including the transmission of light through the tooth and reflectance of light from the tooth. The optical sensor must be configured to detect light having a wavelength at or similar to the wavelength(s) of light emitted by the first and second light sources. In the case of infrared light, the optical sensor must be configured to detect infrared light. According to an embodiment, the optical sensor is a silicon charged-couple device (Si CCD) imaging sensor. However, many other arrangements are possible, including a camera or other optical sensor.

Imaging device 10 further comprises a controller 20. Controller 20 may be formed of one or multiple modules, and is configured to operate imaging device 10 in response to an input, such as input obtained via an actuation button or other user or user-independent activation. Controller 20 can comprise, for example, a processor 22 and a memory 24. Processor 22 may take any suitable form, including but not limited to a microcontroller, multiple microcontrollers, circuitry, a single processor, or plural processors. Memory 24 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by controller 20, controls operation of the hardware components of imaging device 10.

Imaging device 10 may comprise a user interface 18, which could be utilized to provide information to the user. User interface 18 refers to an interface between the imaging device or other device and a human user or operator to enable communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

According to an embodiment, the user interface 18 can provide information to the user about one or more caries detected by the imaging device. The information can be provided as a map of the user's mouth with caries identified, or as a list of caries by tooth number, among many other methods of transmitting this information. According to an embodiment, for example, the feedback mechanism may provide audible and/or tactile feedback, such as a beep or a vibration, in real-time as caries are detected.

Imaging device 10 may comprise one or more additional sensors 26. Sensor 26 may be located anywhere within the device, including for example within the handle or within an extension configured to fit within the user's mouth during use. According to one embodiment, sensor 26 can be integral to controller 20. Sensor 26 can comprise, for example, an inertial motion sensor such as an accelerometer, gyroscope, or magnetic sensor. According to an embodiment, sensor 26 is configured to provide readings of six axes of relative motion (three axes translation and three axes rotation), using for example a 3-axis gyroscope and a 3-axis accelerometer. As another example, sensor 26 is configured to provide the readings of nine axes of relative motion using, for example, 3-axis gyroscope, a 3-axis accelerometer, and a 3-axis magnetometer. Other sensors may be utilized either alone or in conjunction with these sensors, including but not limited to a pressure sensor and other types of sensors, such as a capacitive sensor, a clock, a timer, and other types of sensors. Many different types of sensors could be utilized, as described or otherwise envisioned herein. According to an embodiment, sensor 26 is configured to generate information indicative of the acceleration and angular orientation of imaging device 10. The sensor may comprise two or more sensors 26 that function together as the 6-axis or a 9-axis spatial sensor system. Using sensor 26, for example, the imaging device 10 may obtain information utilized to determine where within the user's mouth the device is located. This information could be utilized to provide feedback to the user about the location of detected caries, among many other uses.

Imaging device 10 may also comprise a connectivity module 28 configured and/or programmed to receive and/or transmit data from or to a wireless transceiver (not shown). For example, connectivity module 28 may transmit sensor data or information about detected caries via a Wi-Fi connection over the internet or an intranet to a separate device, a computer application such as a smartphone application, a dental professional, a database, or other location. Alternatively, connectivity module 28 may receive and/or transmit sensor or feedback data via a Bluetooth or other wireless connection from or to a local device (e.g., a separate computing device), database, or other transceiver. For example, connectivity module 28 allows the user to transmit sensor data to a separate database to be saved for long-term storage, to transmit sensor data for further analysis, to transmit user feedback to a separate user interface, or to share data with a dental professional, among other uses. Connectivity module 28 may also be a transceiver that can receive user input information, such as an instruction to obtain sensor information. Other communication and control signals described herein can be effectuated by a hard wire (non-wireless) connection, or by a combination of wireless and non-wireless connections.

Figure 2:
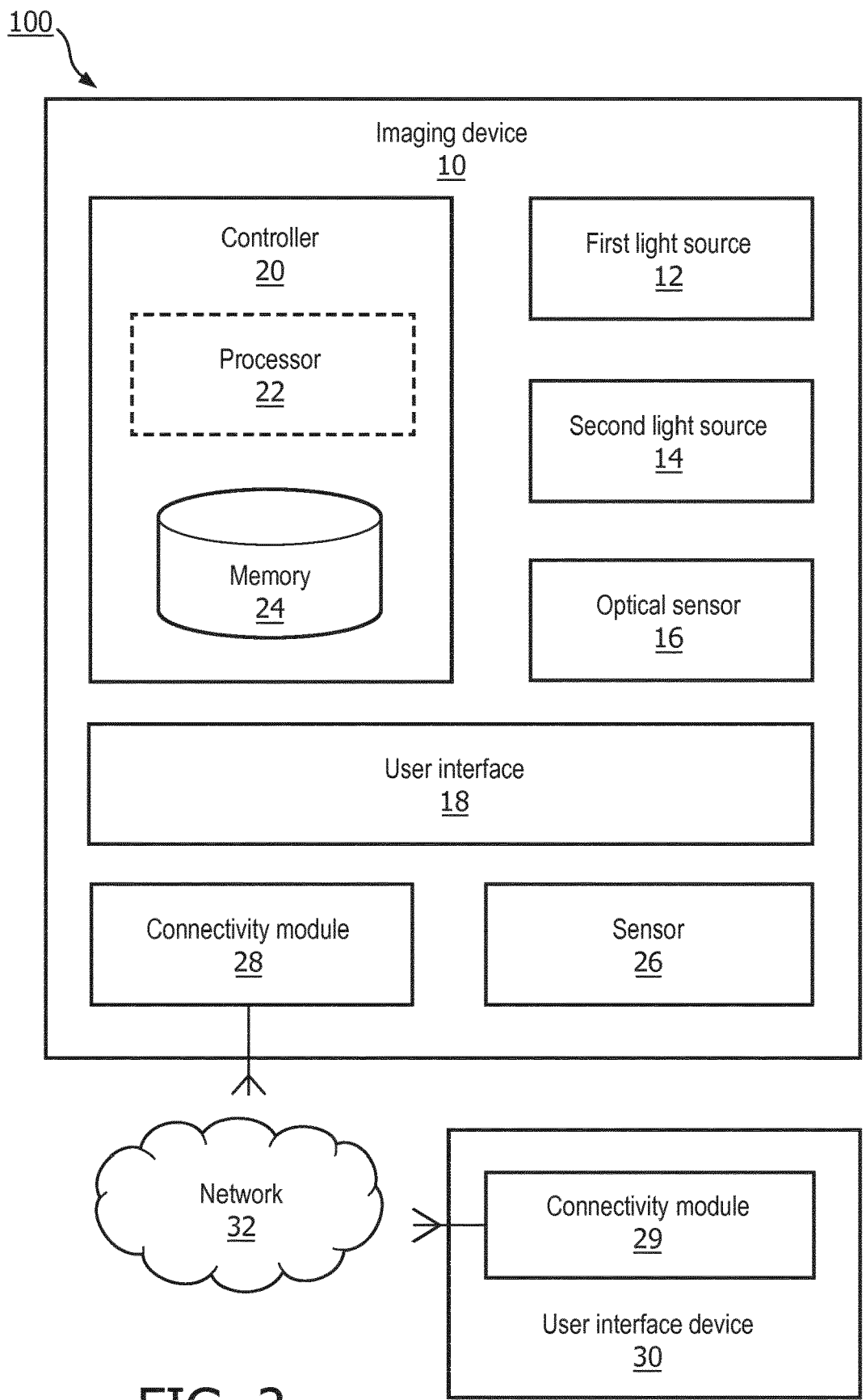
FIG. 2 is a schematic representation of an imaging device system, in accordance with an embodiment.

Referring to FIG. 2, an imaging device system 100 is configured to use light transmission through and reflectance from a tooth to improve the detection of caries, and to communicate information about caries to a user or other individual such as a dental professional. System 100 comprises an imaging device 10, such as the imaging device described with regard to FIG. 1, among other possible imaging devices. Accordingly, the imaging device may comprise first light source 12 and second light source 14, an optical sensor 16, a controller 20 with processor 22 and memory 24, and a connectivity module 28.

System 100 also comprises a user interface device 30 which is designed or configured to provide information to the user about caries detected within a user's mouth. According to an embodiment, user interface device 30 is a computer such as a desktop, laptop, wearable device, smartphone, or other computing device. The user interface device 30 may be a charging station, smart mirror, or other device configured to communicate information to the user. The device may comprise a software application that utilizes information from the imaging device to identify, map, or otherwise provide information to the user about caries detected within a user's mouth.

User interface device 30 further comprises a connectivity module 29 configured and/or programmed to receive and/or transmit data from or to the imaging device 10. Accordingly, system 100 can comprise or be in communication with a network 32 configured to communicate information between connectivity module 28 of the imaging device and connectivity module 29 of the imaging device. The network may be, for example, an internet, intranet, LAN, or any other network. Communication over that network may be wired and/or wireless, and may comprise a Wi-Fi connection, a Bluetooth connection, or any other wired or wireless connection.

Figure 3:
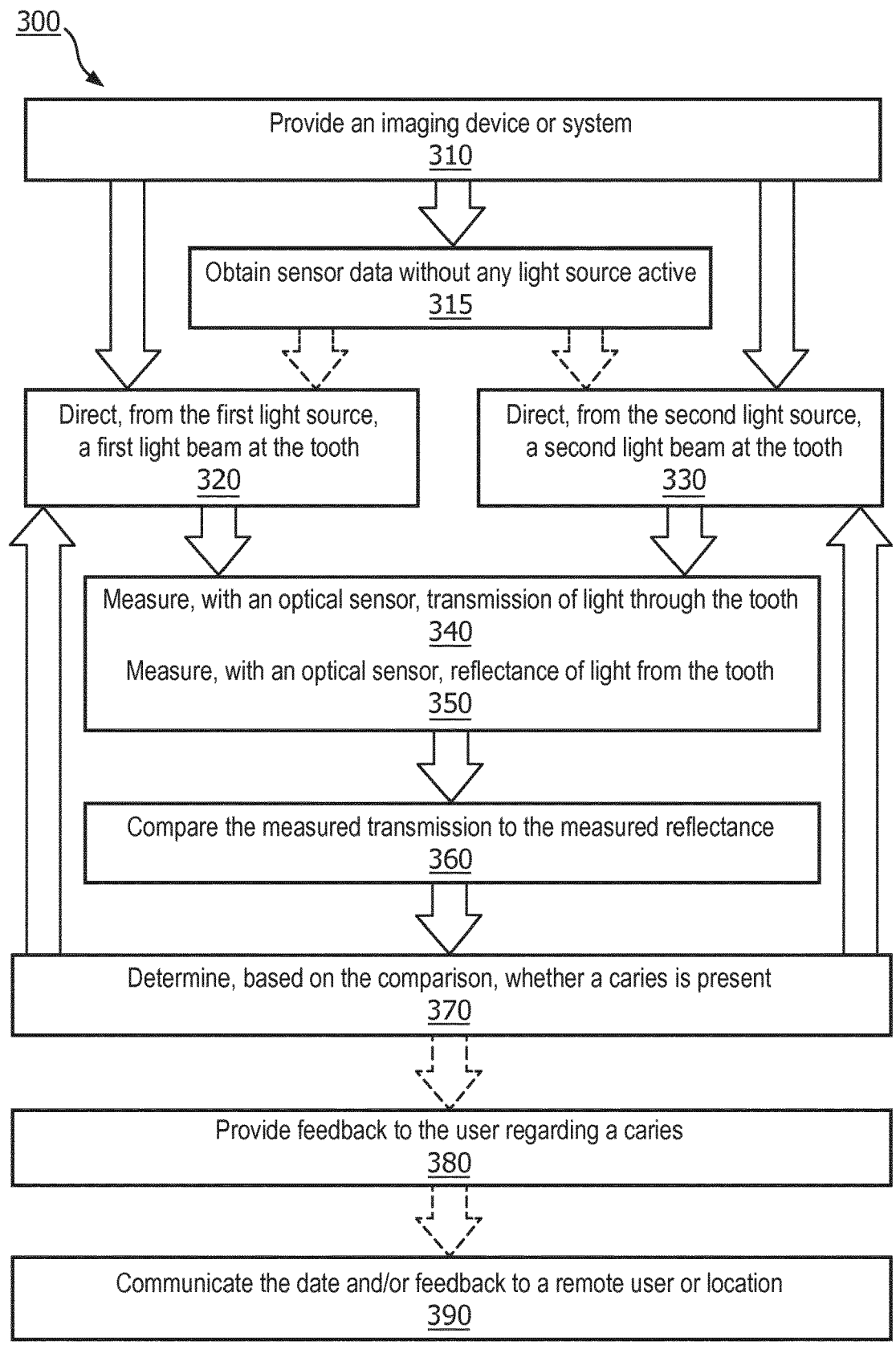
FIG. 3 is a flowchart of a method for detecting caries using an imaging device, in accordance with an embodiment.

Referring to FIG. 3, in one embodiment, is a flowchart of a method 300 for detecting caries using an imaging device in accordance with the present invention.

At step 310 of the method, an imaging device or system configured to detect caries is provided. Imaging device 10 or system 100 can be any of the devices or embodiments described or otherwise envisioned herein. According to an embodiment, imaging device 10 comprises first light source 12 and second light source 14, an optical sensor 16, a controller 20 with processor 22 and memory 24, and a connectivity module 28. Many other configurations and embodiments of imaging device 10 are possible.

At optional step 315 of the method, the device obtains, using the optical sensor, sensor data from the tooth without any active light source. This will detect background light, specular reflection, or any other artifact influencing the optical detector which can be used in subsequent processing steps, as described below.

According to an embodiment, the user positions the imaging device within the mouth and orients the device toward a tooth. According to an embodiment, the device is configured to facilitate proper orientation, and thus may include a guidance tip or other orientation element. The device may be configured to continually emit light and obtain sensor information, or it may be configured to only emit light and/or obtain sensor information when the device is properly positioned or oriented within the user's mouth.

At step 320 of the method, first light source 12 directs a first light beam at a first angle toward a tooth in the user's mouth. The first light beam can be configured to emit infrared light having a wavelength range between 900 nm and 1100 nm, wherein 1000 nm may be an optimal wavelength, although many other light wavelengths, including in ranges other than infrared, may be utilized to illuminate the user's teeth for caries detection.

At step 330 of the method, second light source 14 directs a second light beam at a second angle toward a tooth in the user's mouth, where the second angle is different from the first angle. The second light beam can be configured to emit infrared light having a wavelength range between 900 nm and 1100 nm, wherein 1000 nm may be an optimal wavelength, although many other light wavelengths, including in ranges other than infrared, may be utilized to illuminate the user's teeth for caries detection.

According to an embodiment, one of the first and second light sources is positioned or otherwise configured to illuminate the tooth with light that will be utilized to obtain information about transmission of that light through the tooth, and the other of the first and second light sources is positioned or otherwise configured to illuminate the tooth with light that will be utilized to obtain information about reflectance of that light from the tooth.

The imaging device 10 will co-ordinate steps 320 and 330 as necessary. According to an embodiment, steps 320 and 330 of the method can be performed simultaneously or sequentially. For example, step 330 can follow step 320, or step 320 can follow step 330. The first and second light sources can emit a sustained, flash, or pulsing light beam simultaneously toward the tooth. As another example, first and second light sources can each emit a sustained, flash, or pulsing light beam sequentially or in an alternating or other pattern. For example, the first light source may emit a beam multiple times compared to the second light source, and vice versa.

At step 340 of the method, the optical sensor 16 of imaging device 10 measures transmission of light from one of the first and second light sources through the tooth, and at step 350 of the method, the optical sensor 16 of imaging device 10 measures reflectance from the tooth of light from the other of the first and second light sources. According to an embodiment, steps 340 and 350 of the method can be performed simultaneously or sequentially. For example, step 340 can follow step 350, or step 350 can follow 340. The first and second light sources can emit a sustained, flash, or pulsing light beam simultaneously toward the tooth. As another example, first and second light sources can each emit a sustained, flash, or pulsing light beam sequentially or in an alternating or other pattern. For example, the first light source may emit a beam multiple times compared to the second light source, and vice versa.

According to an embodiment, the optical focus of the light sources is the surface of the tooth. Alternatively, the focal point of the light sources can be just below the surface of the tooth, and thus the optical sensor may comprise means to apply a focus offset as compared to the tooth surface.

The imaging device may immediately proceed to analyze the obtained images, may store the images in memory, and/or may communicate the obtained images to another device or system. For example, the controller of the imaging device may receive the images and immediately analyze the images to provide real-time feedback to the user. As another example, the device may analyze obtained images only after a scanning session is complete and all surfaces to be imaged have been imaged. As yet another example, the device may transmit—continuously or periodically—images to a remote computer or server. Additionally, the system may store the obtained images for historical comparisons or other long-term analyses.

At step 360 of the method, the imaging device compares the measured transmission to the measured reflectance. For example, processor 22 of controller 20 of the imaging device receives the obtained images directly or from memory 24, and analyzes the images to identify caries. According to an embodiment, the processor compares the measured transmission at a location of a tooth to the measured reflectance at that location. The processor can utilize one or more algorithms to compare the measured transmission at a location of a tooth to the measured reflectance at that location. For example, "R" can represent the measured pixel value for reflected light at a first position, and "T" can represent the measured pixel value for transmitted light at that first position. For each pixel, the processor can calculate a value for that pixel and location using the following equation:

$$(R-T)/(R+T) \quad \text{(Eq. 1)}$$

According to an embodiment, the signal processing using Equation 1 is based on the insight that reflection at a caries spot is higher, and transmission at a caries spot is lower than a reflection from an area of the tooth without caries. Accordingly, through this signal processing an improved method for caries detection is provided, and absorption artifacts due to effects such as staining are suppressed.

According to an embodiment, the processor is configured to improve caries detection by correcting for background light and other artifacts. Prior to signal processing using Equation 1, the processor can correct each pixel value of R and/or T using sensor data obtained when there is no illumination from any light source. If there is background light or any other artifact influencing the optical detector, the sensor data obtained when there is no illumination from any light source will detect this influence.

At optional step 315 of the method, the device may have obtained sensor data from the tooth without any active light source to detect background light, specular reflection, or any other artifact influencing the optical detector. At step 315 and/or at step 360 of the method, the processor will perform an offset correction for one or more pixel values using sensor data. For example, the processor can correct R and T for each pixel by subtracting the obtained background data, or by otherwise utilizing the offset values.

At step 370 of the method, the imaging device determines, based on the comparison from step 360, whether a caries is present in the tooth. According to an embodiment, a certain value of the comparison, such as a value from Equation 1 or another evaluation may indicate an increased probability or likelihood of a caries. For example, the processor may compare the values from the comparison in step 360 to a predetermined or preprogrammed threshold, determine that a caries is present or likely present if the comparison values exceed the threshold or fall within a threshold range. Alternatively, the processor may utilize historical data at each pixel location by comparing a current pixel value to a past pixel value, and can determine that a caries is present based on changes to the location over time. According to another embodiment, the processor may utilize comparison data from multiple locations along a tooth, and can determine that a caries is present based on comparison data differences between locations on that tooth. Many other methods for determining a caries is present based on the comparison data from step 360 are possible.

At optional step 380 of the method, the imaging device or system can provide feedback or other information to the user about one or more caries, or the lack thereof. For example, the imaging device or system can provide feedback or other information to the user via a user interface. The feedback or other information can be provided to the user in real-time, following a scanning session, or at any other time. According to an embodiment, the feedback is provided to the user via a wired or wireless network connection to a smartphone, a computer program, a base station, a remote software service, or via other means. The information can be provided as a map of the user's mouth with caries identified, or as a list of caries by tooth number, among many other methods of transmitting this information. According to an embodiment, for example, the feedback mechanism may provide audible and/or tactile feedback, such as a beep or a vibration, in real-time as caries are detected. According to another embodiment, the feedback can also be utilized to present information to a dental professional for diagnosis which is subsequently communicated back to the user, either in real-time or delayed.

At optional step 390 of the method, feedback or other information about one or more caries is communicated to a remote individual, device, and/or location. For example, the information can be provided directly to a healthcare professional such as a dentist or dental hygienist. For example, information about one or more scanning sessions can be stored and transmitted to a healthcare professional automatically or upon request. According to an embodiment, the information can be stored on the user's smartphone and then brought to the dental professional's office during a visit, where the information is automatically uploaded via a Bluetooth connection. The dental professional can then review the feedback and utilize that information during care.

Figure 4:
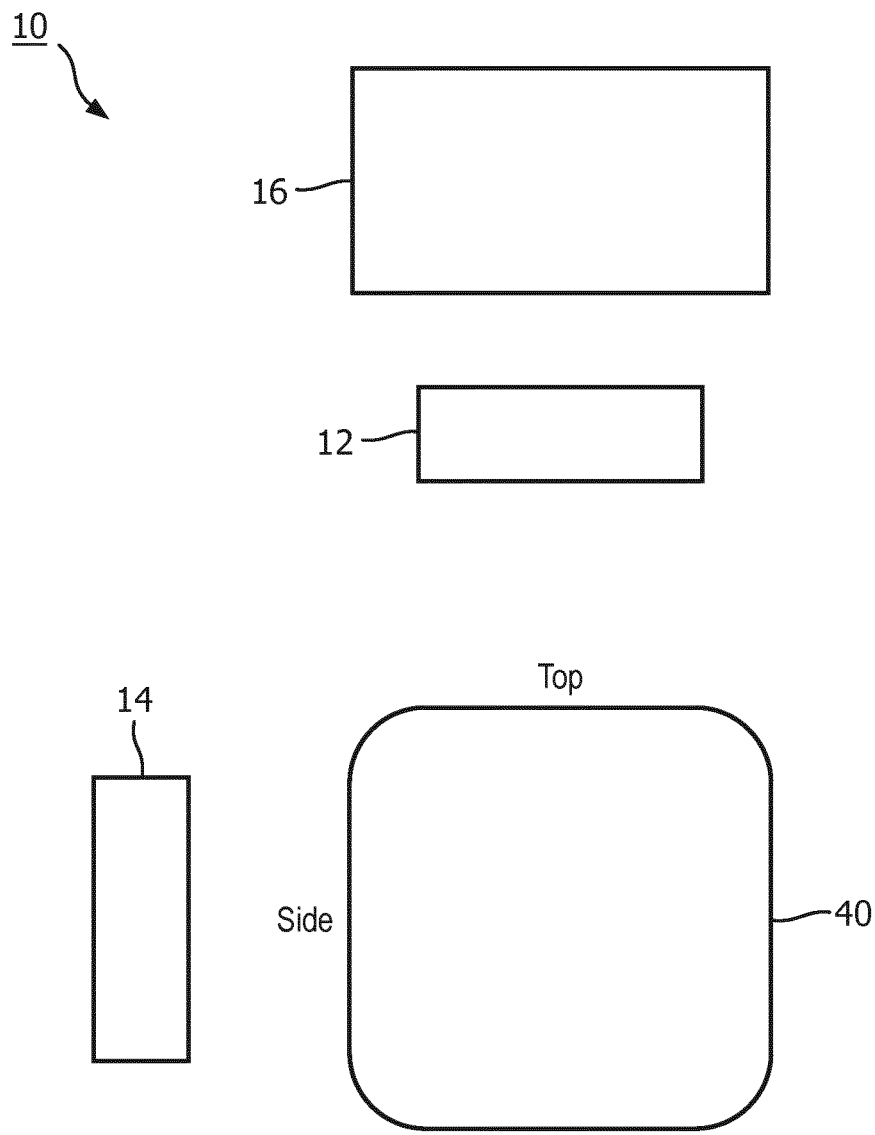
FIG. 4 is a schematic representation of an imaging device positioned around a tooth, in accordance with an embodiment.
Figure 5:
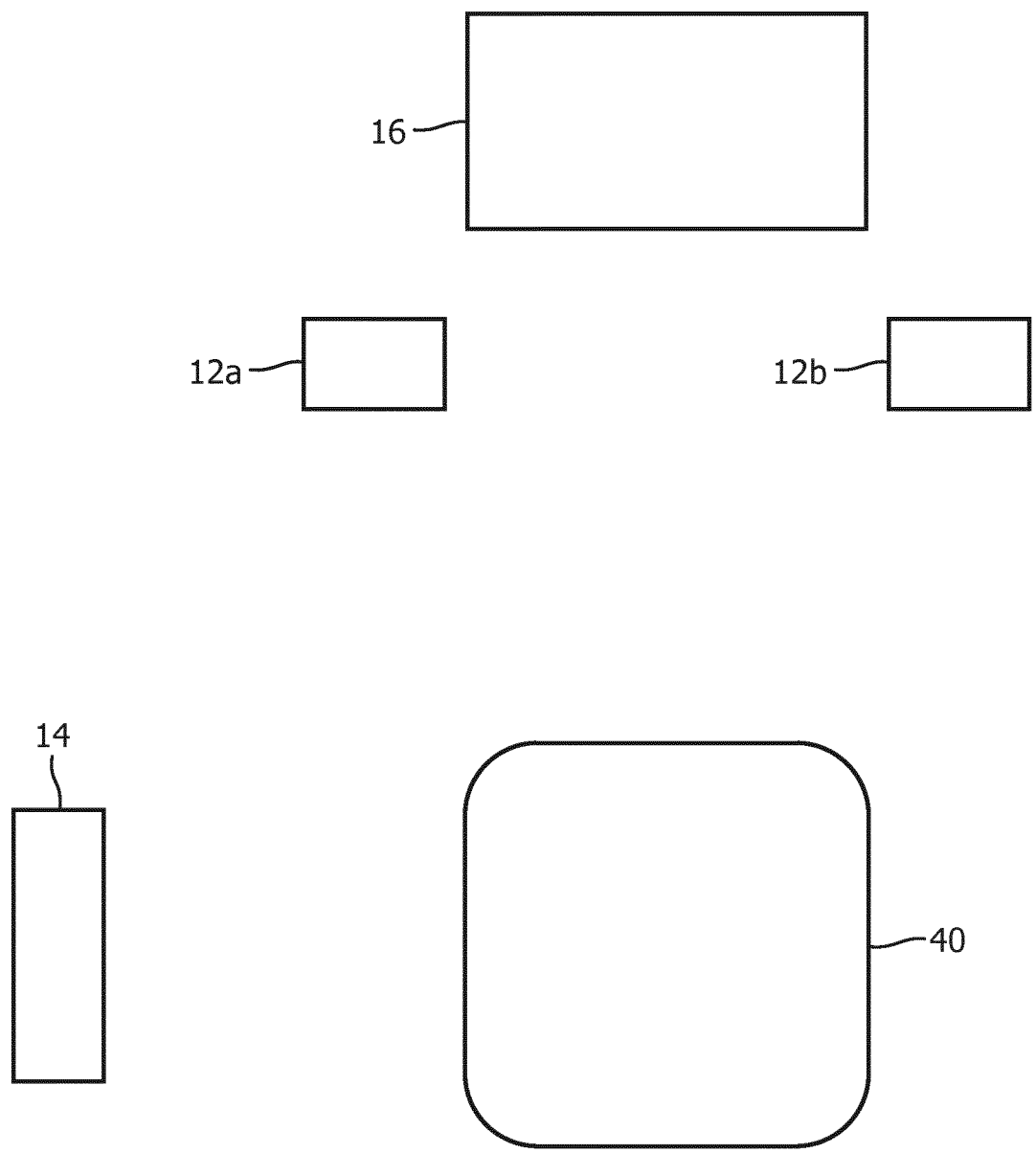
FIG. 5 is a schematic representation of an imaging device positioned around a tooth, in accordance with an embodiment.

Referring to FIG. 4, in one embodiment, are components of an imaging device 10 positioned around a tooth 40. The imaging device includes a first light source 12, a second light source 14, and an optical sensor 16. In this configuration, at least one of the first and second light sources is configured to emit light that illuminates a surface of the tooth, and the optical sensor can detect the reflectance of the light off that surface. Additionally, at least one of the first and second light sources is configured to emit light that at least partially penetrates and then exits the tooth, and the optical sensor can detect the transmission of that light through the tooth. As described or otherwise envisioned herein, many other configurations of imaging device 10 are possible. According to an embodiment, light source 12 may be positioned to one side of optical sensor 16 to allow light from the light sources to be detected by the optical sensor. Additionally, one or both of light sources 12 and 14 may be two or more light sources, as shown for example in FIG. 5, in which light source 12 comprises light sources 12a and 12b.

Figure 6:
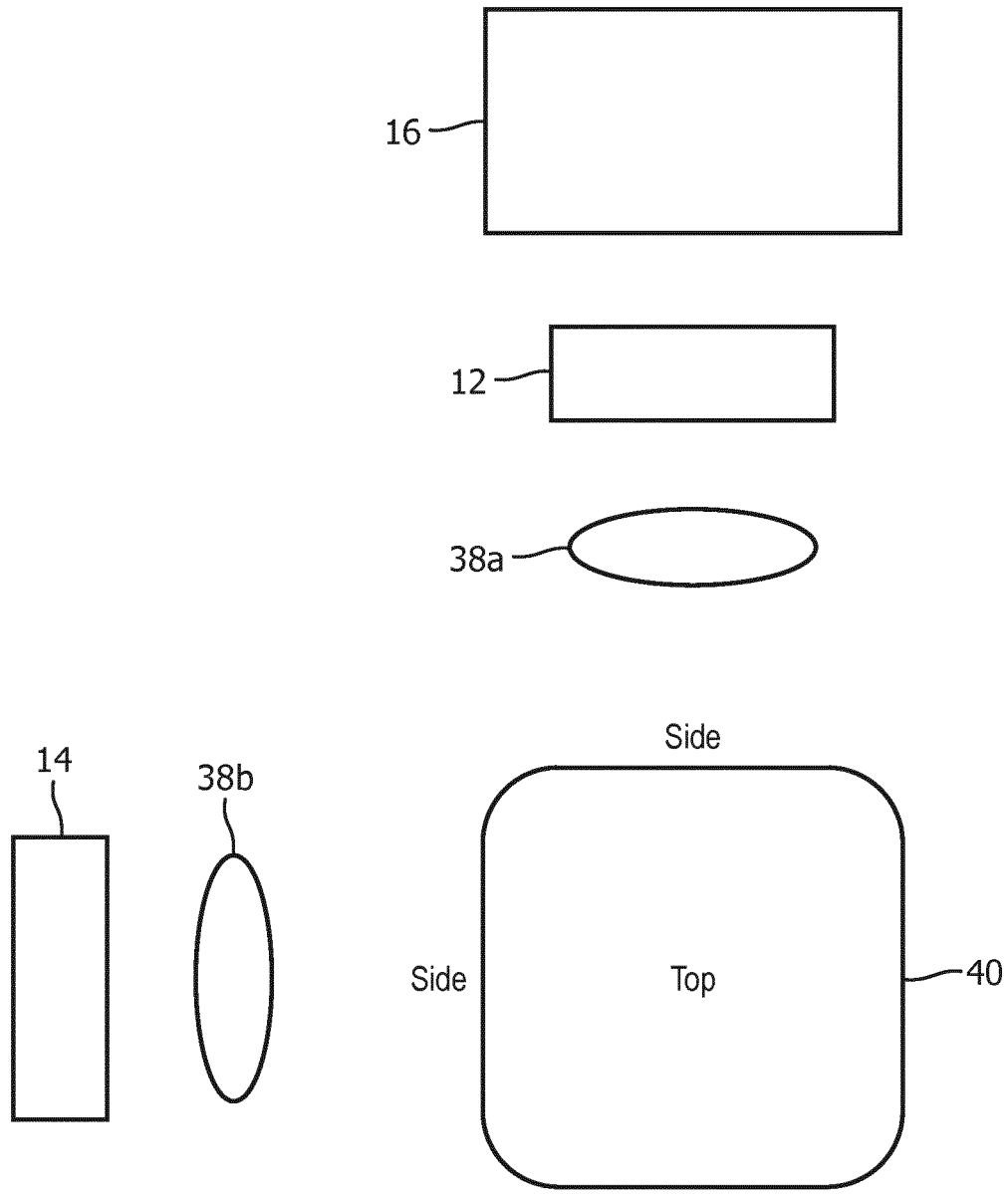
FIG. 6 is a schematic representation of an imaging device positioned around a tooth, in accordance with an embodiment.

Referring to FIG. 6, in one embodiment, are components of an imaging device 10, positioned around a tooth 40, with a first light source 12, a second light source 14, and an optical sensor 16. In this configuration, one or both of the first and second light sources includes an optical element 38a, 38b such as a lens, polarizer, or other optical element. For example, a lens may focus light on a particular portion or region of the tooth, and/or a polarizer may be used to eliminate specular reflections from the tooth surface.

Figure 7:
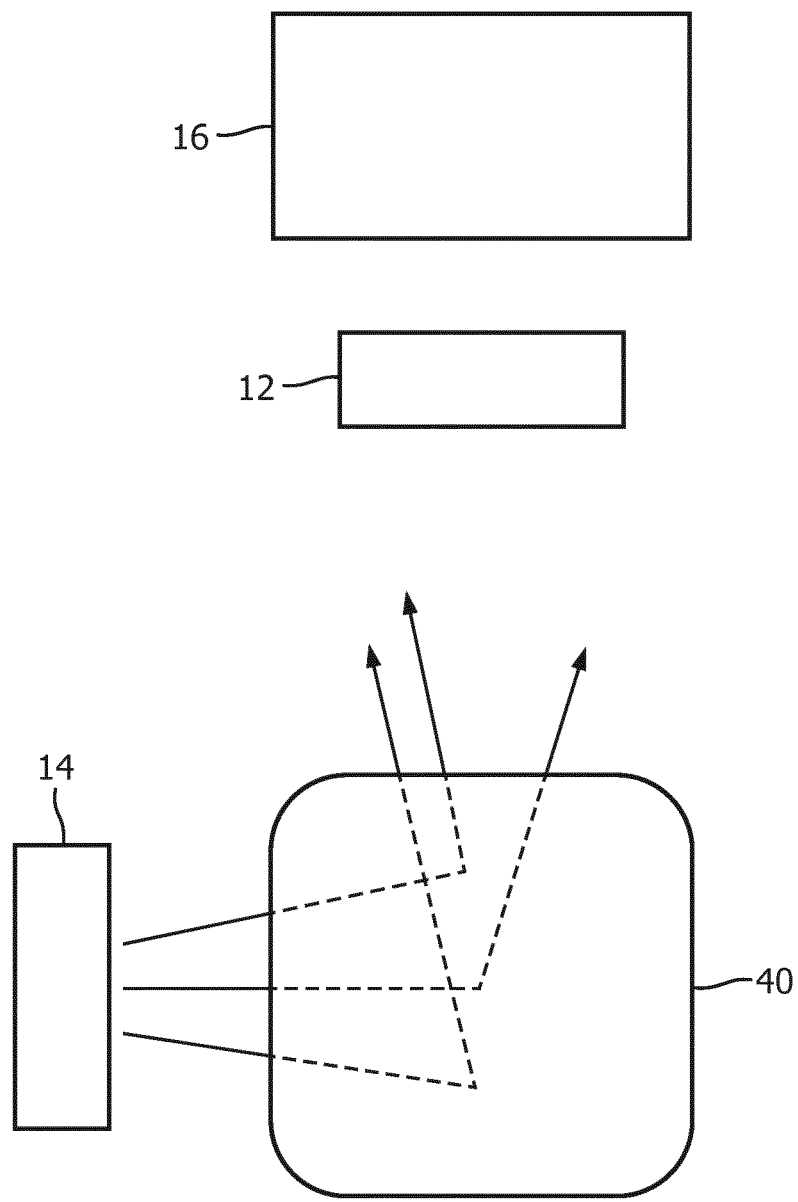
FIG. 7 is a schematic representation of an imaging device positioned around a tooth, in accordance with an embodiment.
Figure 8:
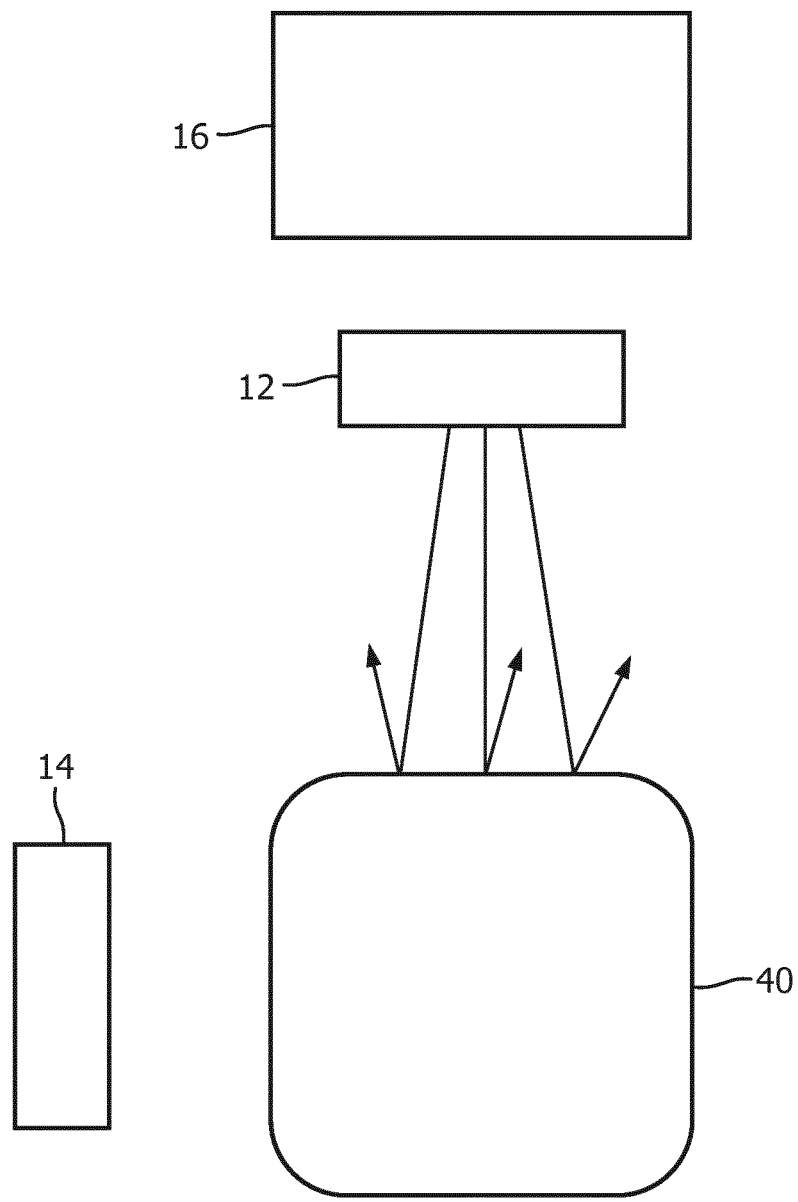
FIG. 8 is a schematic representation of an imaging device positioned around a tooth, in accordance with an embodiment.

Referring to FIG. 7, in one embodiment, imaging device 10 is positioned around tooth 40, in which light source 14 is emitting light toward tooth 40. The light is at least partially transmitted through tooth 40, and the optical sensor 16 detects this transmission. Similarly, referring to FIG. 8, in one embodiment, imaging device 10 is positioned around tooth 40, in which light source 12 is emitting light toward tooth 40. The light is at least partially reflected off the surface of tooth 40 and optical sensor 16 detects this reflectance.

According to an embodiment, for a measurement of reflection, the tooth is illuminated from the top using one or two light sources, such as LEDs, and the optical sensor stores a picture of the top of the tooth. After that, the tooth is trans-illuminated by another LED, giving a small vertical illumination area on the teeth and a large horizontal illumination area. This may be provided or enhanced by a lens. This light is being scattered by the dentin and partly directed towards the camera system, and a second image is stored. Alternatively, a second LED for side illumination might be positioned on the other side of the tooth as well to achieve a more homogeneous illumination. For offset correction of stray light and the detector, an image of the tooth can be obtained with the light sources inactive.

Figure 9:
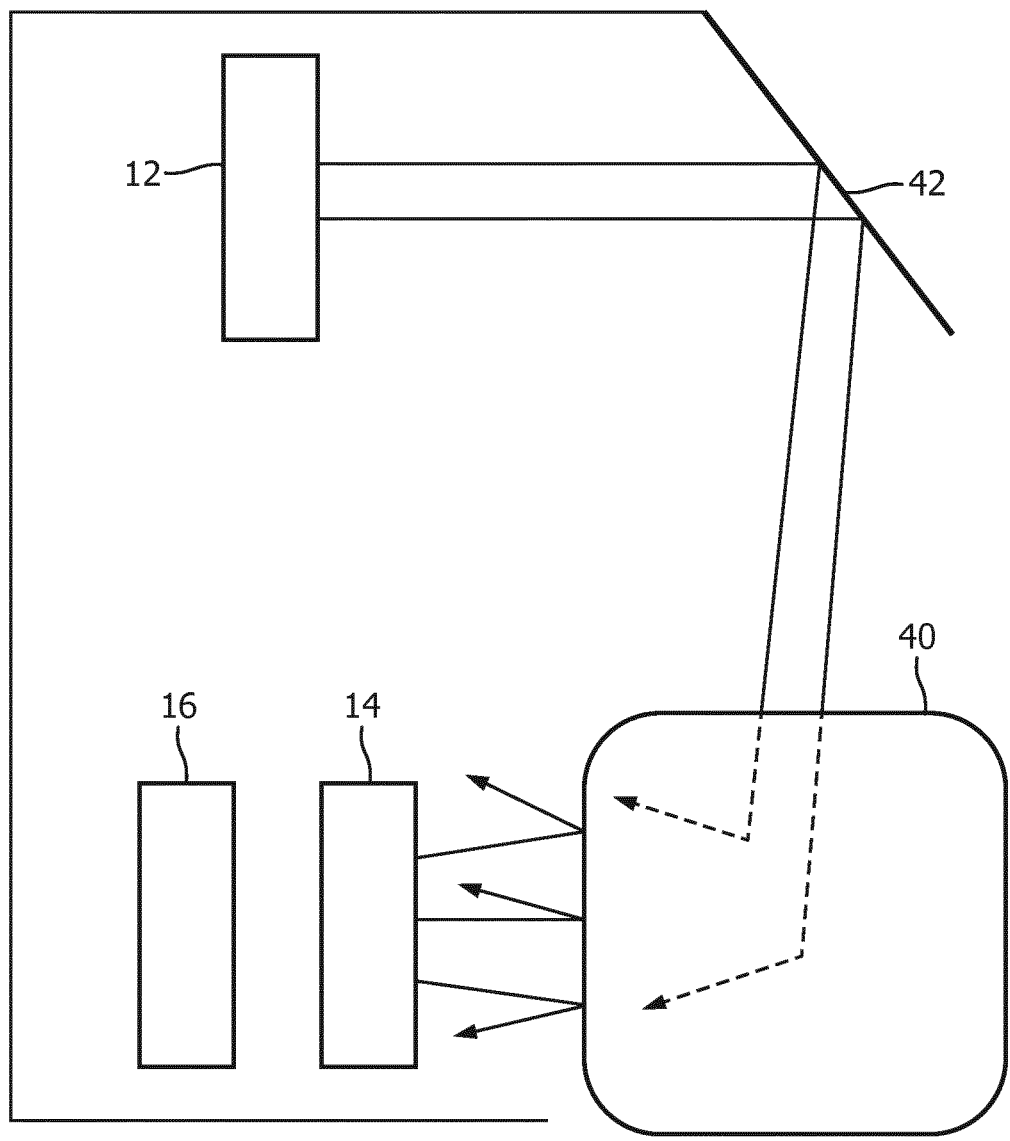
FIG. 9 is a schematic representation of an imaging device positioned around a tooth, in accordance with an embodiment.

Referring to FIG. 9, in one embodiment, are components of an imaging device 10 positioned around a tooth 40. The imaging device includes a first light source 12, a second light source 14, and an optical sensor 16. In this configuration, light source 12 is configured to emit light that trans-illuminates tooth 40 and is detected by optical sensor 16. Light source 14 is configured to illuminate a surface of the tooth, and the optical sensor detects the reflectance of the light off that surface. In this configuration, the imaging device further comprises a mirror 42 which facilitates directing of light from light source 12. Light source 12 emits light toward the mirror, which redirects the light toward tooth 40 where it can trans-illuminate the tooth and be detected by optical sensor 16. This mirror configuration may allow the imaging device to be more compact and user-friendly, or may allow improved visualization of the tooth.

Figure 10:
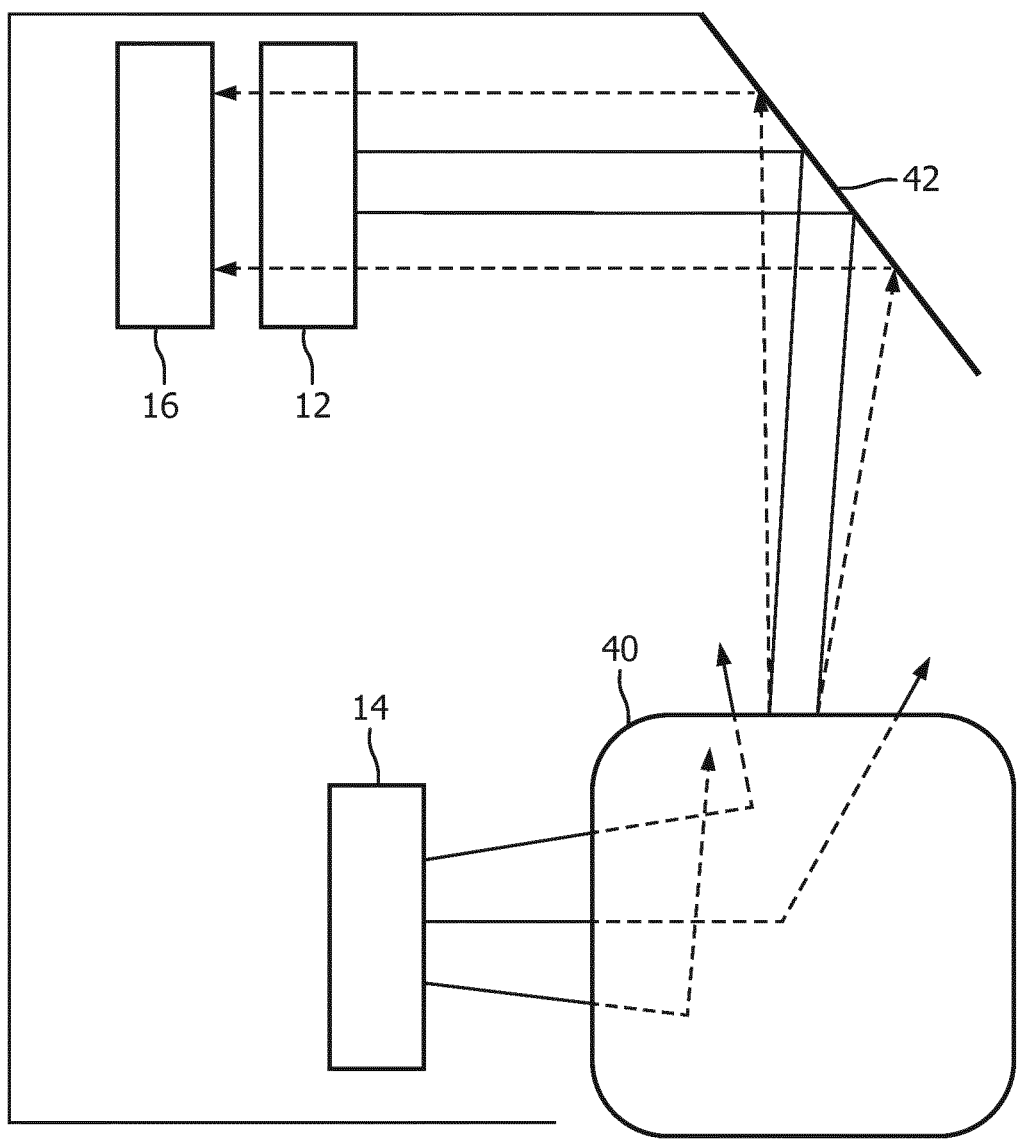
FIG. 10 is a schematic representation of an imaging device positioned around a tooth, in accordance with an embodiment.

Similarly, in FIG. 10, mirror 42 is configured and/or positioned to reflect light both to and from the tooth. Light source 12 emits light toward the mirror, which redirects the light toward tooth 40 where it can reflect off the surface of the tooth back toward the mirror and the optical sensor. Light source 14 emits light toward the tooth 40 where it can trans-illuminate the tooth, and at least some of that light will be directed toward the mirror 42 and subsequently the optical sensor 16.

Figure 11:
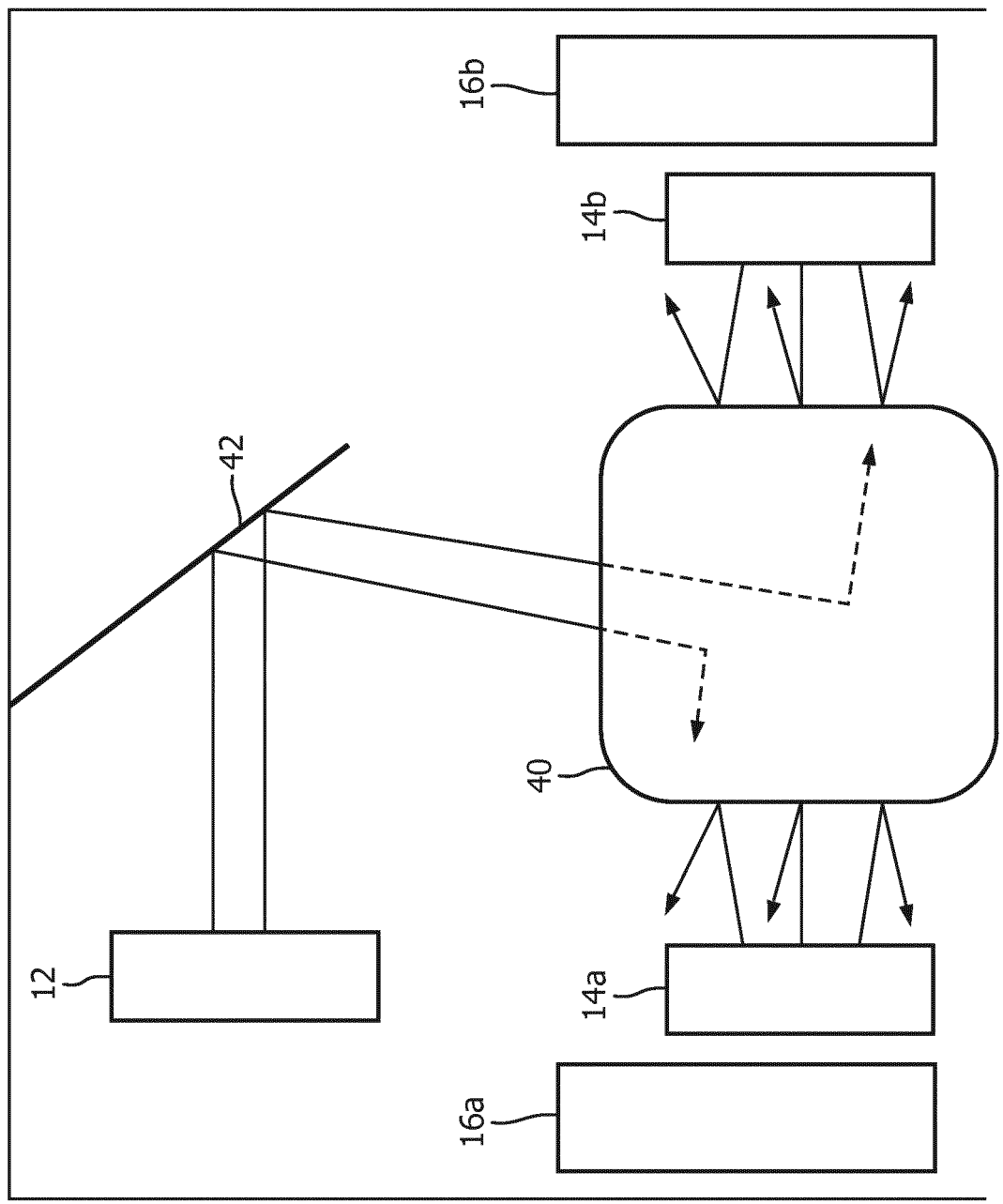
FIG. 11 is a schematic representation of an imaging device positioned around a tooth, in accordance with an embodiment.

Referring to FIG. 11, in one embodiment, are components of an imaging device 10 positioned around a tooth 40. The imaging device includes a first light source 12, a second light source 14a and 14b, and an optical sensor 16a and 16b. In this configuration, light source 12 is configured to emit light that trans-illuminates tooth 40 and is detected by one or both optical sensors 16a and 16b. Light sources 14a and 14b are configured to emit light that reflects off a surface of tooth 40 to be detected by optical sensors 16a and 16b. Light sources 12 and 14, as well as 14a and 14b, may emit light simultaneously or sequentially. According to an embodiment, the imaging device in FIG. 11 may be mounted on a structure similar to a toothbrush handle, and can be manually moved along the teeth as it emits light and obtains sensor information.

In one or more embodiments of the imaging device 10, the device may be structured or configured to minimize the space needed by the device between the upper and lower teeth, thereby increasing the comfortability and use of the device. For example, the imaging device may comprise multiple optical sensors to image multiple sides of the tooth at one time, thereby saving time and promoting use of the device.

In each of FIGS. 9-11, although all light sources are shown emitting light simultaneously, it should be understood that they may be emitting light simultaneously, in a sequential pattern, or in any other order or pattern. For example, one light may emit light to be detected by the optical sensor, and then a second light may emit light to be detected by the optical sensor, but only after the first light is no longer emitting a light beam.

According to another embodiment, the imaging system may be utilized with other systems or mechanisms to further enhance the user's feedback and information. For example, the imaging device or system may comprise fluorescent imaging, such as 405 nm excitation and 630 nm detection, as well as red excitation and NIR detection, one or more of which can be utilized for the enhanced detection of mature biofilms as found in dentinal caries and at interproximal locations.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for detecting one or more caries using an imaging device, the method comprising the steps of:

directing light from a first light source toward a tooth;

measuring, with an optical sensor, transmission of light from the first light source through the tooth and obtaining a transmission value for a pixel of the transmission at a first position;

directing light from a second light source toward the tooth, wherein the second light source directs light at the tooth at a different angle relative to the first light source;

measuring, with the optical sensor, reflectance from the tooth of light from the second light source and obtaining a reflection value for a pixel of the reflectance at the first position;

comparing the transmission value to the reflectance value and obtaining a comparison value for a location of the tooth; and determining, based on the comparison value, whether a caries is present in the tooth.

2. The method of claim 1, further comprising the step of obtaining, with the optical sensor, sensor data without light from the first and the second light source, and wherein said comparing step further comprises subtracting the sensor data obtained without light from the measured transmission and/or the measured reflectance.

3. The method of claim 1, wherein the optical sensor is an image sensor, and wherein said determining step is further based on a local variation of the transmission value and the reflection value for one or more pixels.

4. The method of claim 1, further comprising the step of providing the determination of whether a caries is present in the tooth to a user.

5. The method of claim 1, further comprising the step of communicating the determination of whether a caries is present in the tooth to a remote user or device.

6. The method of claim 1, wherein at least one of said first or second light sources is a fluorescent light source.

7. The method of claim 1, wherein said first and second light sources emit light having a wavelength between 900 and 1100 nm.

8. An imaging device configured to detect one or more caries, the device comprising:

an optical sensor;

a first light source configured to direct light toward a tooth such that the optical sensor measures transmission of light from the first light source through the tooth;

a second light source configured to direct light toward the tooth such that the optical sensor measures reflectance from the tooth of light from the second light source; and a controller configured to: (i) obtain a transmission value for a pixel of the transmission at a first position, and obtain a reflection value for a pixel of the reflectance at the first position; (ii) compare the transmission value to the reflectance value and obtain a comparison value for a location of the tooth; and (iii) determine, based on the comparison value, whether a caries is present in the tooth.

9. The imaging device of claim 8, wherein the second light source directs light at the tooth at a different angle relative to the first light source.

10. The imaging device of claim 8, further comprising a user interface configured to provide the determination of whether a caries is present in the tooth to a user.

11. The imaging device of claim 8, wherein the optical sensor is further configured to obtain sensor data without light from the first and second light source, and wherein the controller is configured to subtract the sensor data obtained without light from the first or second light source from the measured transmission and/or the measured reflectance.

12. The imaging device of claim 8, wherein said first and second light sources emit light having a wavelength between 900 and 1100 nm.

13. An imaging system configured to provide a user with information about one or more caries, the system comprising:

an imaging device comprising: (i) an optical sensor; (ii) a first light source configured to direct light toward a tooth such that the optical sensor measures transmission of light from the first light source through the tooth; (iii) a second light source configured to direct light toward the tooth such that the optical sensor measures reflectance from the tooth of light from the second light source; (iv) a controller configured to obtain a transmission value for a pixel of the transmission at a first position and obtain a reflection value for a pixel of the reflectance at the first position, compare the transmission value to the reflectance value, obtain a comparison value for a location of the tooth, and determine, based on the comparison value, whether a caries is present in the tooth; and (v) a connectivity module configured to communicate the determination; and a user interface device comprising: (i) a connectivity module configured to receive the communicated determination; and (ii) a user interface configured to provide the determination of whether a caries is present in the tooth to the user.

14. The imaging system of claim 13, wherein the optical sensor is further configured to obtain sensor data without light from the first and second light source, and wherein the controller is configured to subtract the sensor data obtained without light from the measured transmission and/or the measured reflectance.

15. The imaging system of claim 13, wherein said first and second light sources emit light having a wavelength between 900 and 1100 nm.

\* \* \* \* \*